US009409031B2

(12) United States Patent
Lindner et al.

(10) Patent No.: US 9,409,031 B2
(45) Date of Patent: Aug. 9, 2016

(54) MEDICAL DEVICES INCLUDING FLEXIBLE CIRCUIT BODIES WITH EXPOSED PORTIONS OF CIRCUIT TRACES ATTACHED TO ELECTRICAL CONTACTS OF COMPONENTS

(75) Inventors: Gerald G. Lindner, Lino Lakes, MN (US); William C. Phillips, Brooklyn Park, MN (US); Dominique Piguet, Epalinges (CH); Daniel T. Pyne, Chandler, AZ (US); Micah A. Litow, Evanston, IL (US); James Strom, Arden Hills, MN (US); Mark G. Wosmek, Ramsey, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 247 days.

(21) Appl. No.: 13/069,019

(22) Filed: Mar. 22, 2011

(65) Prior Publication Data

US 2011/0257711 A1    Oct. 20, 2011

Related U.S. Application Data

(60) Provisional application No. 61/319,861, filed on Mar. 31, 2010.

(51) Int. Cl.
*A61N 1/375* (2006.01)

(52) U.S. Cl.
CPC ......... *A61N 1/3752* (2013.01); *Y10T 29/49117* (2015.01)

(58) Field of Classification Search
CPC ... A61N 1/0472; A61N 1/0476; A61N 1/375; A61N 1/3752; A61N 1/3754

USPC ...................................................... 607/72, 116
See application file for complete search history.

(56) References Cited

U.S. PATENT DOCUMENTS

| 3,566,005 | A | | 2/1971 | Shaheen |
| 4,430,522 | A | * | 2/1984 | Bader ............................. 29/854 |
| 4,654,102 | A | | 3/1987 | Wery et al. |
| 5,620,476 | A | * | 4/1997 | Truex et al. ..................... 607/36 |
| 5,750,926 | A | * | 5/1998 | Schulman et al. ............ 174/564 |
| 7,380,961 | B2 | | 6/2008 | Moriyama et al. |
| 2003/0233133 | A1 | * | 12/2003 | Greenberg et al. ............. 607/36 |
| 2005/0119709 | A1 | * | 6/2005 | Gauglitz et al. ................ 607/36 |
| 2008/0107897 | A1 | | 5/2008 | Hwang et al. |
| 2009/0124965 | A1 | * | 5/2009 | Greenberg et al. ............. 604/67 |

* cited by examiner

*Primary Examiner* — Joseph Dietrich
(74) *Attorney, Agent, or Firm* — Withers & Keys, LLC

(57) ABSTRACT

Medical devices include stimulation and/or sensing circuitry that is interconnected to electrical components by a flexible circuit body having exposed portions of circuit traces that are attached to electrical contacts of the electrical components. Each circuit trace may span a separate window formed in an insulative body of the flexible circuit body, or a plurality of circuit traces may span a single window or may be freely extending from the insulative body. The exposed portion of the circuit trace may be plated with a conductive metal and then attached to the electrical contact of the electrical component. The flexible circuit body may be an extension from a flexible electrical circuit board containing the circuit. The circuit may be present on a circuit board that includes electrical contacts and where the flexible circuit body has exposed portions of circuit traces attached to the electrical contacts of the circuit board.

24 Claims, 7 Drawing Sheets

MEDICAL DEVICES INCLUDING FLEXIBLE CIRCUIT BODIES WITH EXPOSED PORTIONS OF CIRCUIT TRACES ATTACHED TO ELECTRICAL CONTACTS OF COMPONENTS

RELATED CASES

The present application claims priority to U.S. Provisional Patent Application No. 61/319,861, filed Mar. 31, 2010, which is incorporated herein in its entirety.

TECHNICAL FIELD

Embodiments relate to medical devices that include flexible circuit bodies. More particularly, embodiments relate to medical devices that include flexible circuit bodies having exposed portions of circuit traces that are attached to electrical contacts of components.

BACKGROUND

Medical devices such as implantable pulse generators typically include a primary circuit board that contains various electronic devices such as microcontrollers, waveform generators, and the like. These electronic devices may be used to create stimulation signals that provide therapy to a patient in some cases, this circuit board may be of a flexible nature while in other cases this circuit board may be rigid or semi-rigid.

Various other electronic components of the medical device may be located separately from the circuit board. For instance, a battery may be present and have a connection point where the electrical contacts of the battery are present. Likewise, a stimulation capacitor may be present and have a connection point where the electrical contacts of the capacitor are present. A feedthrough interconnect may be present to provide a conductive pathway for stimulation signals to be passed outside of the sealed housing of the device and the feedthrough may have a connection point where electrical contacts are present.

The primary circuit board relies on the interconnections to these various other electronic components. Conventionally, one or more flexible circuit bodies are used to provide this interconnection. However, these flexible circuit bodies include relatively large ribbon conductors that have been bonded or otherwise attached to the flexible circuit bodies to establish electrical connections to circuit traces within the flexible circuit bodies. These relatively large ribbon conductors on one end of the flexible circuit body may then be bonded or otherwise attached to relatively large electrical contacts on the primary circuit board while relatively large ribbon conductors on the opposite end of the flexible circuit body may then be bonded or otherwise attached to relatively large electrical contacts of the other components.

This conventional approach to interconnecting the primary circuit board to the various other electrical components has several drawbacks. For instance, the addition of the ribbon conductors to the flexible circuit body requires steps necessary to add these additional parts. This process introduces costs, time, and potential faults into the construction of the flexible circuit body.

Furthermore, these ribbon conductors are relatively large, often on the order of 5 to 10 thousandths of an inch thick. The bond pads that receive these ribbon conductors are in proportion to the ribbon conductors and therefore are relatively large as well. The relatively large size of these ribbons thereby constrains efforts to miniaturize the medical device.

SUMMARY

Embodiments address issues such as these and others by providing for attachment of the circuit traces of the flexible circuit body to electrical contacts of the electrical components of the medical device. The circuit traces have portions that are exposed from an insulative body of the flexible circuit body and those portions are attached to the electrical contacts to create an electrical connection between the circuit traces and the electrical contacts of the electrical components.

Embodiments provide a method of constructing a medical device. The method involves providing a flexible circuit body having at least one conductive circuit trace with an insulative body covering the at least one conductive circuit trace, the at least one conductive circuit trace having a portion that is exposed from the insulative body, the at least one conductive circuit trace being electrically coupled to a first circuit that produces stimulation signals. The method further involves attaching the portion of the circuit trace that is exposed from the insulative body to an electrical contact associated with an electrical component by a resistive weld to create an electrical connection between the portion of the circuit trace and the electrical contact.

Embodiments provide a medical device that includes a housing and a first circuit within the housing that generates stimulation pulses. The medical device further includes an electrical component within the housing and spaced from the first circuit, the electrical component having an electrical contact. Additionally, the medical device includes a flexible circuit body within the housing and having at least one conductive circuit trace with an insulative body covering the at least one conductive circuit trace, the at least one conductive circuit trace having a portion that is exposed from the insulative body and that is attached to the electrical contact of the electrical component by a resistive weld to create an electrical connection between the portion of the circuit trace and the electrical contact of the electrical component, and the circuit trace being electrically coupled to the first circuit.

Embodiments provide a method of providing stimulation therapy from a medical device having a pulse generator circuit and having a feedthrough located separately from the pulse generator circuit. The method involves generating stimulation pulses by the pulse generator circuit and conducting the stimulation pulses from the pulse generator circuit to a circuit trace of a flexible circuit body. The method further involves passing the signals from the circuit trace of the flexible circuit body to an electrical contact of the feedthrough, the circuit trace including a portion exposed from an insulative body of the flexible circuit body such that the portion of the circuit trace is attached to the electrical contact of the feedthrough by a resistive weld. The method further involves carrying the signals from a lead conductor electrically coupled to the feedthrough to the electrode.

Embodiments provide a method of constructing a medical device that involves providing a flexible circuit body having at least one conductive circuit trace with an insulative body covering the at least one conductive circuit trace, the at least one conductive circuit trace having a portion that is exposed from the insulative body, the at least one conductive circuit trace being electrically coupled to a first circuit that produces stimulation signals, the exposed portion having a same width as a remainder of the circuit trace within the insulative body, though in some embodiments, the exposed portion has a different width as the remainder of the circuit trace within the insulative body. The method further involves attaching the portion of the circuit trace that is exposed from the insulative body to an electrical contact associated with an electrical component to create an electrical connection between the portion of the circuit trace and the electrical contact.

Embodiments provide a medical device that includes a housing, a first circuit within the housing that generates stimulation pulses, and an electrical component within the housing and spaced from the first circuit, the electrical component having an electrical contact. The medical device further includes a flexible circuit body within the housing and having at least one conductive circuit trace with an insulative body covering the at least one conductive circuit trace, the at least one conductive circuit trace having a portion that is exposed from the insulative body and that is attached to the electrical contact of the electrical component to create an electrical connection between the portion of the circuit trace and the electrical contact of the electrical component. The exposed portion has a same width as a remainder of the circuit trace within the insulative body, and the circuit trace is electrically coupled to the first circuit, though in some embodiments, the exposed portion has a different width as the remainder of the circuit trace within the insulative body.

Embodiments provide a method of providing stimulation therapy from a medical device having a pulse generator circuit and having a feedthrough located separately from the pulse generator circuit. The method involves generating stimulation pulses by the pulse generator circuit and conducting the stimulation pulses from the pulse generator circuit to a circuit trace of a flexible circuit body. The method further involves passing the signals from the circuit trace of the flexible circuit body to an electrical contact of the feedthrough, the circuit trace including a portion exposed from an insulative body of the flexible circuit body such that the portion of the circuit trace is attached to the electrical contact of the feedthrough, the exposed portion having a same width as a remainder of the circuit trace within the insulative body, though in some embodiments, the exposed portion has a different width as the remainder of the circuit trace within the insulative body. The method further involves carrying the signals from a lead conductor electrically coupled to the feedthrough to the electrode.

DETAILED DESCRIPTION

Embodiments provide for the connection of a circuit of a medical device to an electrical component spaced from the circuit by using a flexible circuit body that includes circuit traces with exposed portions. The exposed portions of the circuit traces may be attached directly to electrical contacts of the electrical components, thereby eliminating the need to add separate ribbon conductors to the flexible circuit body.

Figure 1:
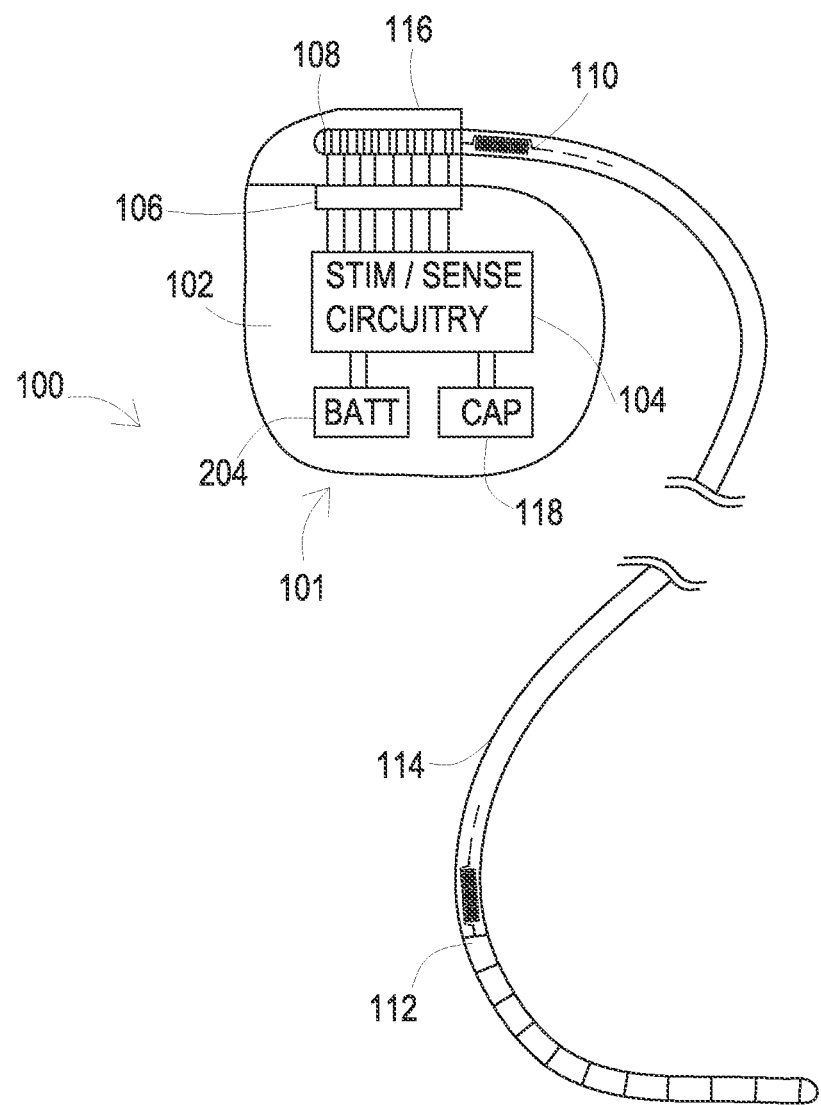
FIG. 1 shows a medical system that includes a medical lead connected to a medical device having a flexible circuit body according to various embodiments.

FIG. 1 shows an implantable medical system 100 that includes a medical device 101 having a housing 102 that contains circuitry 104 for providing medical tasks such as stimulation or physiological sensing. The circuitry 104 includes electrical interconnections to a feedthrough 106 that passes the electrical signals to connections 108 within a header block 116 of the medical device 101. The connections 108 are where connectors of the header block 116 contact connectors of a medical lead 114. The circuitry 104 also includes electrical interconnections to other electrical components such as a battery 204 and a capacitor 118.

The medical lead includes conductors 110 which are coils in this example. These conductors 110 carry signals between the connections 108 within the header block 116 and electrodes 112 on a distal end of the medical lead 114. These electrodes 112 may be used to deliver stimulation signals being generated by the circuitry 104 to adjacent tissue of a patient and/or to sense physiological signals from the adjacent tissue and provide those to the circuitry 104.

Figure 5:
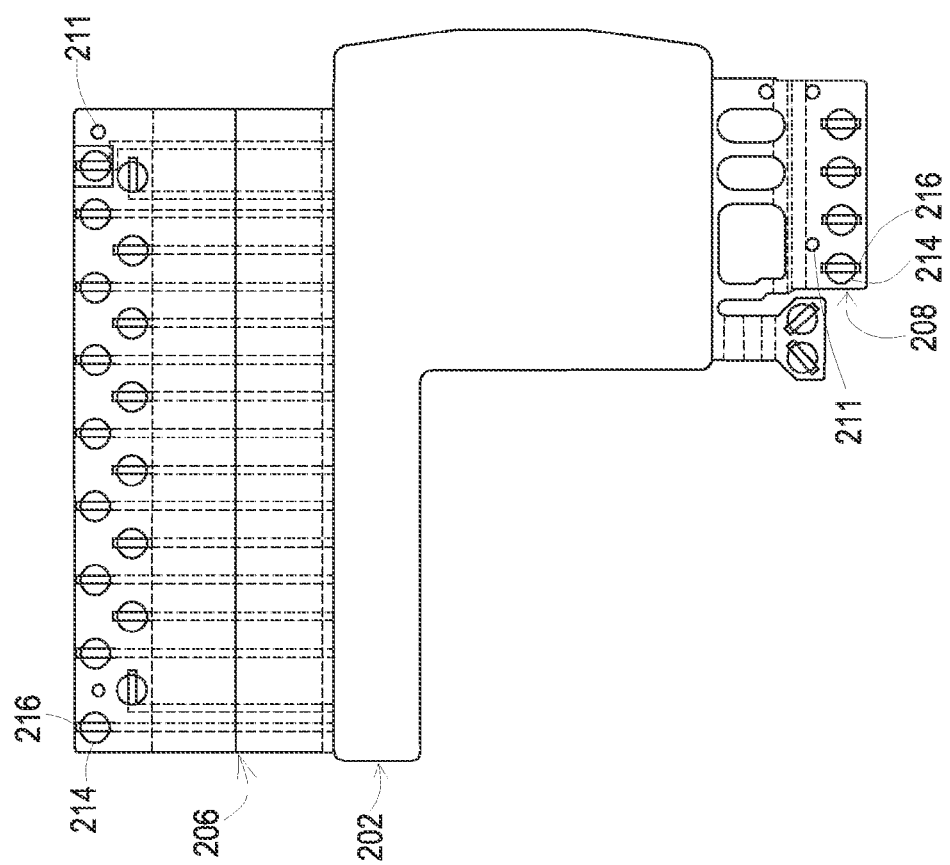
FIG. 5 shows flexible circuit bodies integrated into a primary circuit board of the medical device according to various embodiments.
Figure 6:
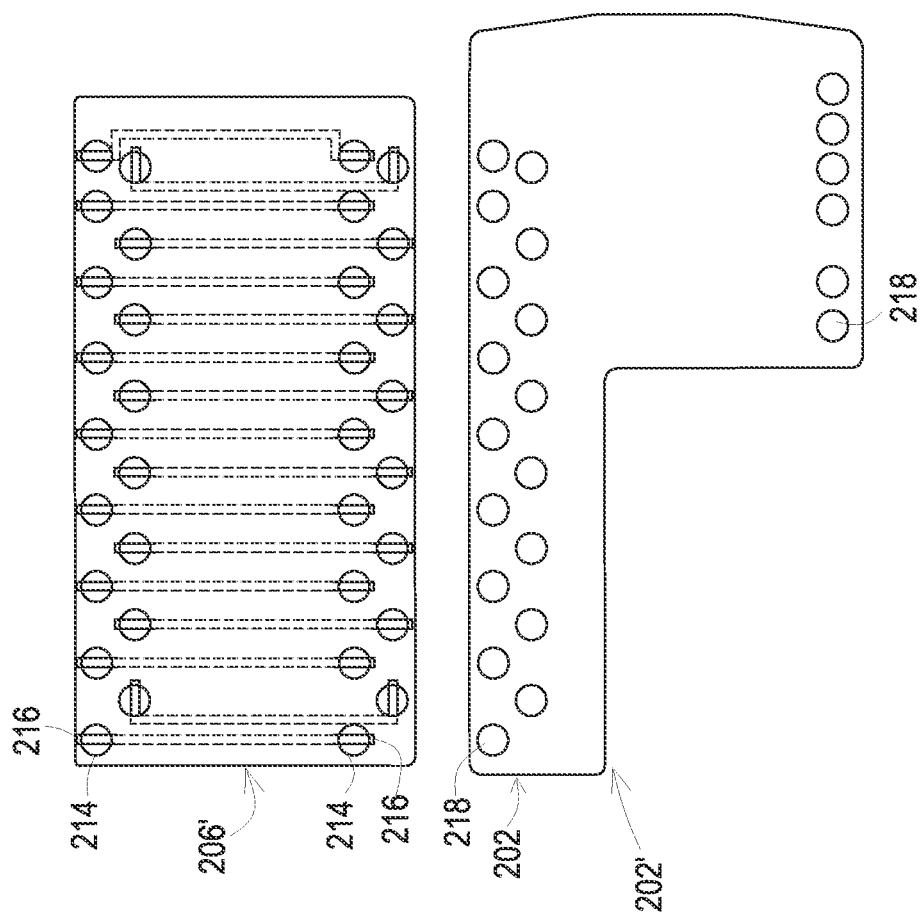
FIG. 6 shows a flexible circuit body separate from a primary circuit board of the medical device according to various embodiments.
Figure 7:
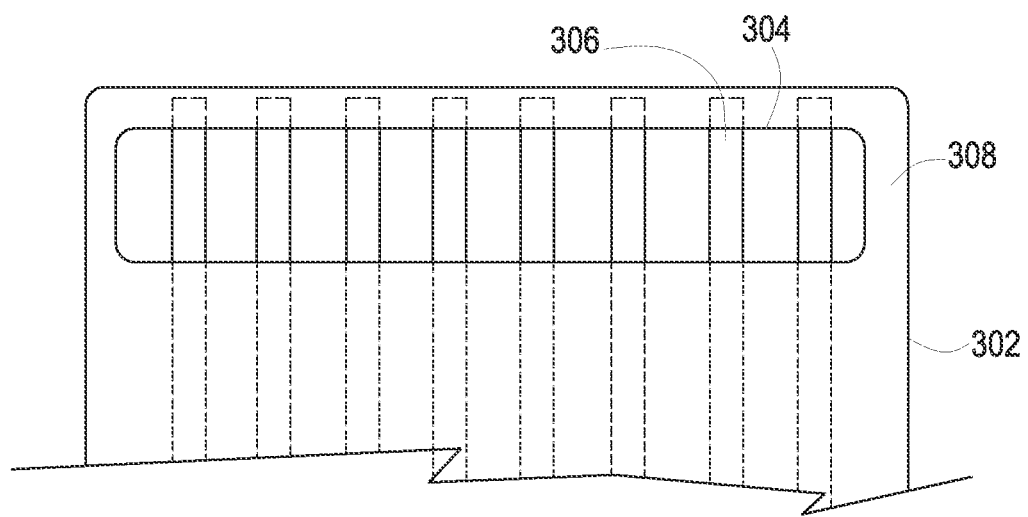
FIG. 7 shows an end of a flexible circuit body having multiple circuit trace portions exposed within a single window according to various embodiments.

The circuitry 104 relies on various electrical components such as the feedthrough 106 to provide the medical therapy and these electrical components may be spaced from the circuitry 104 within the housing 102. To provide the interconnection of the circuitry 104 to the various electrical components, flexible circuit bodies may be included that provide one or more circuit traces that conduct the stimulation or sensed signals. These circuit traces are shown in FIGS. 5-7 that are discussed in more detail below.

Figure 2:
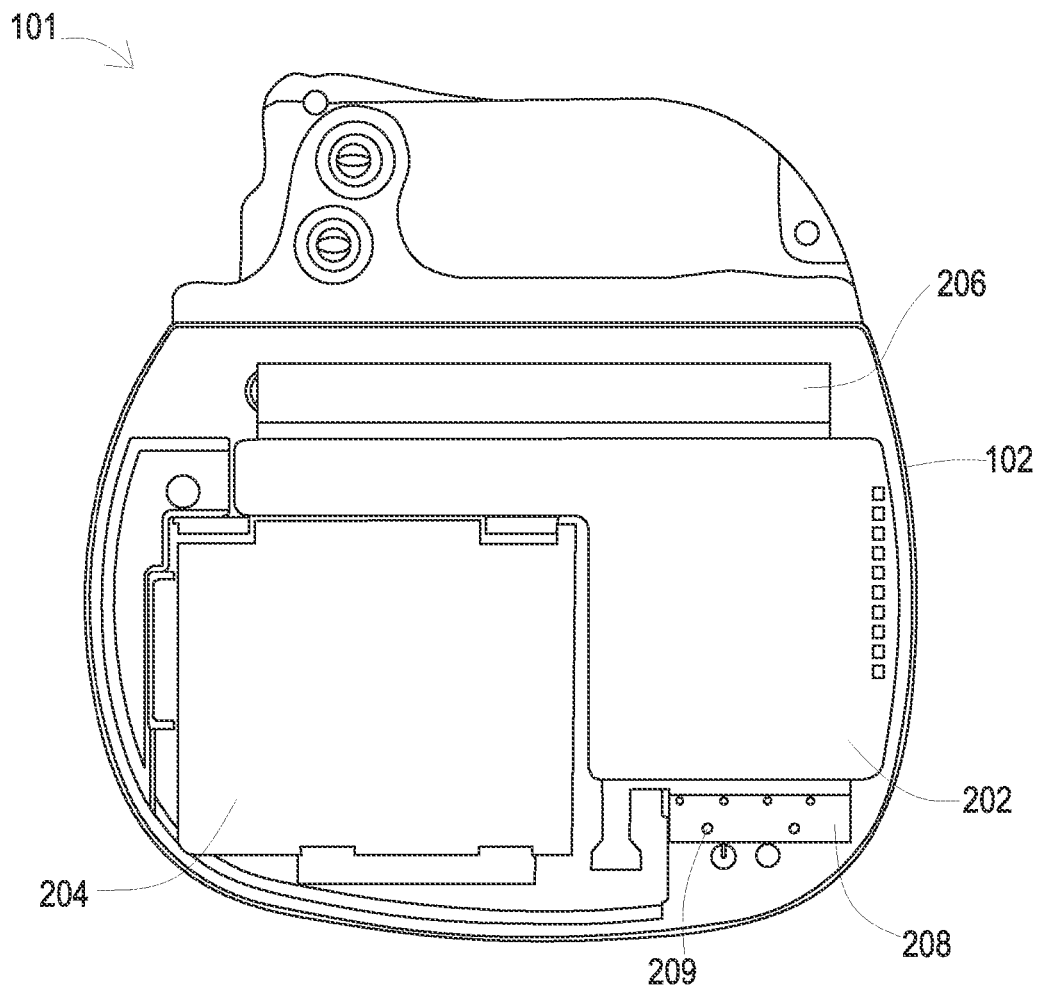
FIG. 2 shows a front view of the medical device having a side of a housing removed to reveal the flexible circuit body according to various embodiments.
Figure 3:
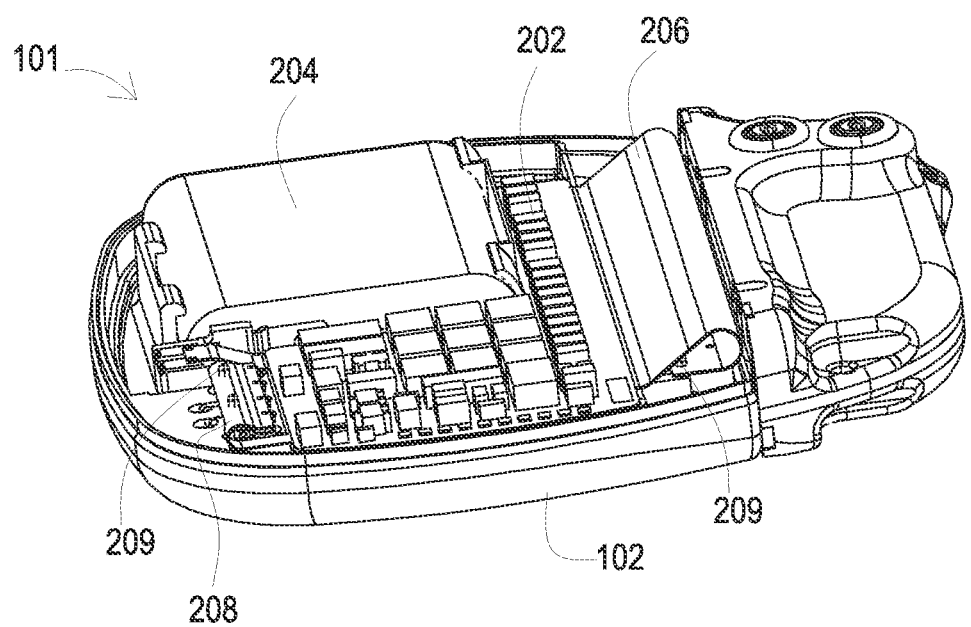
FIG. 3 shows a side view of the medical device having the side of the housing removed to reveal the flexible circuit body according to various embodiments.
Figure 4:
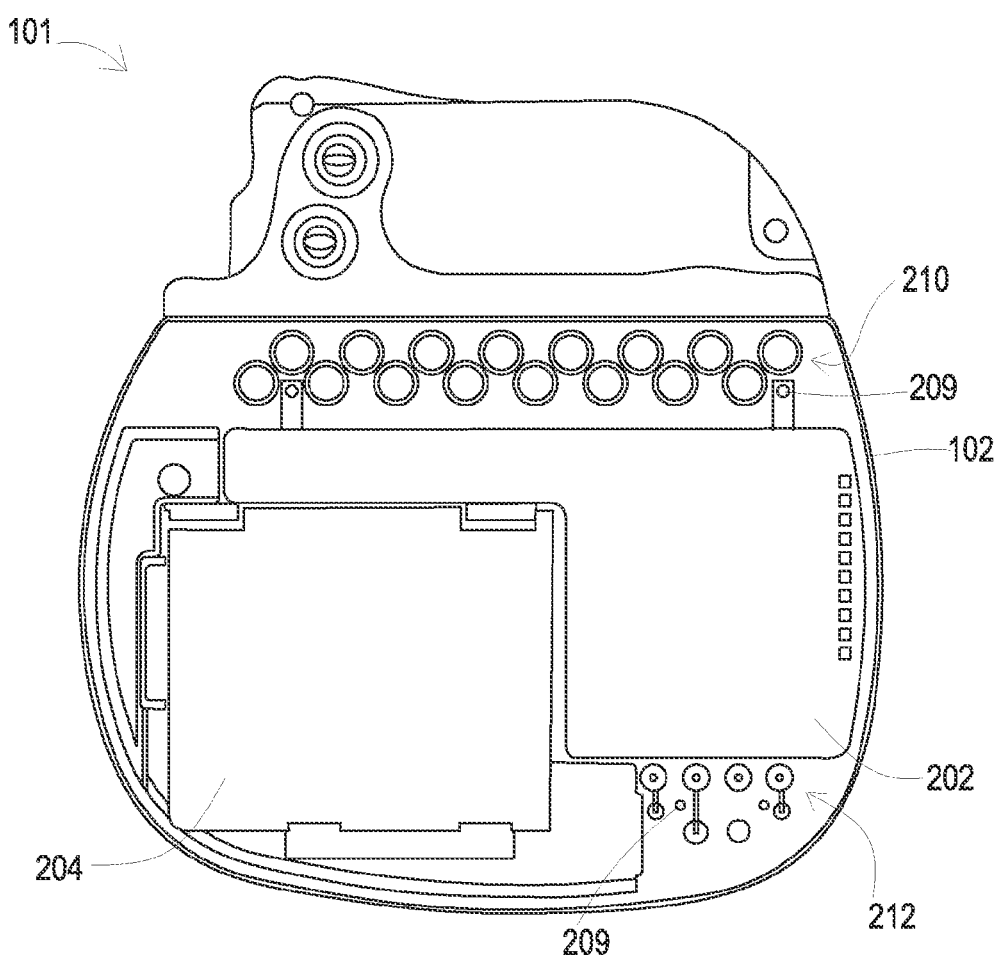
FIG. 4 shows a front view of the medical device having the side of the housing removed and having the flexible circuit bodies removed to reveal electrical contacts of electrical components.

FIGS. 2 and 3 show an example of a medical device 101 with a front half of the housing 102 removed to reveal various items including flexible circuit bodies 206 and 208 according to various embodiments. FIG. 4 shows the example of the medical device with the flexible circuit bodies 206 and 208 removed to reveal underlying features. In this example, the circuitry 104 of FIG. 1 is located on a separate circuit board 202.

This circuit board 202 is surrounded in this example by other electrical components. These electrical components may include items such as a battery 204, a connection point 212 where electrical contacts of components including the battery 204 and a telemetry antenna are located, a feedthrough 106 having a collection of bond pads 210, and others such as stimulation capacitors.

The flexible circuit bodies 206 and 208 of this example are mated to the circuit board 202 during manufacturing. Circuit traces within the circuit board 202 continue as integral conductors through the flexible circuit bodies 206 and 208. These circuit traces are contained within an insulative body that forms the exterior surface of the flexible circuit bodies 206 and 208. This insulative body may be constructed of materials such as one or more layers of polyimide joined by an adhesive. In such a case, the circuit board 202 may be made of a resin and fiberglass (e.g., FR4) material and the polyimide of the flexible circuit bodies 206 and 208 may be embedded into the circuit board 202 or adhered to it.

It is also an option to utilize a flexible circuit board 202 that may include the flexible circuit bodies 206 and 208 as integral parts. In such a case, the circuit traces of the flexible circuit board 202 continue through the flexible circuit body parts 206 and 208 in the same manner as if the circuit board 202 is rigid.

FIG. 5 shows the circuit bodies 206 and 208 extending from the circuit board 202 such that there are circuit traces that continue as a single piece of material from the circuit board 202 into the flexible circuit bodies 206 and 208. FIG. 5 also shows features of the flexible circuit bodies 206 and 208 that are present at the ends of the flexible circuit bodies 206 and 208 opposite the circuit board 202. Windows 214 are formed in the insulative body of the flexible circuit bodies 206 and 208 to expose portions 216 of the circuit traces present within the insulative body. These portions 216 are part of a one-piece continuous circuit trace that travels across the flexible circuit body 206, 208 within the insulator, as indicated by the phantom lines. These portions 216 may be attached directly to the corresponding electrical contacts 210 of the feedthrough 106 for portions 216 of the flexible circuit body 206 and the connection point 212 for the portions 216 of the flexible circuit body 208. In this manner, there is a direct connection from the integral circuit trace of the flexible circuit body 206, 208 to an electrical contact of an electrical component, thereby avoiding the need to include an intervening lead that would otherwise bridge between the integral circuit trace and the electrical contact.

The windows 214 are formed by removing the insulative material surrounding the portion of the circuit trace to be exposed. Conventional techniques for forming apertures in the insulative material while leaving the exposed portions of the circuit traces intact may be used. For example, the window may be created by laser cutting so that the exposed portions 216 are left in place to span the windows 214. Furthermore, while the windows 214 are circular in this particular example, other shapes are also applicable. Also, as discussed below in relation to FIG. 7, exposed portions of multiple circuit traces may be present within a single window rather than providing a separate window for each exposed portion and may also be exposed by freely hanging from an end of the insulator body rather than spanning a window within the insulator body.

The circuit traces of the flexible circuit body 206 are typically constructed of copper. The exposed portions 216 of the circuit traces may be plated with a conductive material such as nickel or gold to assist with the attachment of the exposed portions 216 to the bond pads or other types of electrical contacts. Any suitable conductive material, such as, for example, titanium, valadium, or platinum, or the like, may be plated onto the circuit traces. For instance, in an example embodiment, nickel or gold plating may protect the copper trace during a process of attaching the exposed portion 216 to the electrical contact of a component by using a resistive weld, particularly a resistive spot weld where the plating also becomes attached to the electrical contact of the electrical component. Furthermore, particularly for copper traces, in some embodiments it may be desirable to first plate the copper circuit trace with nickel and then plate gold over the nickel so that the gold diffusion into the copper trace is limited or eliminated. While a resistive weld is an effective form of attachment, any other suitable forms of attachment such as, for example, ultrasonic welding, laser welding, wire bonding, and soldering are also applicable.

The circuit trace, including the exposed portion 216, may be made relatively small. Reducing the size of the attachment between the flexible circuit body and the electrical contact of a component assists in miniaturizing the medical device 102. For instance, the thickness of the exposed portion 216 after being plated with nickel or copper may be relatively small, such as on the order of 12 to 18 micrometers. The width may be proportionally small as well, such as on the order of 250 to 400 micrometers. It will be appreciated that other thicknesses and widths are also applicable. Furthermore, the width of the exposed portion 216 may be the same as the remainder of the circuit trace within the flexible circuit body 206, 208, as shown in the figures, or may have a different width.

The relatively small nature of the exposed portions provides other benefits in addition to assisting in miniaturizing the medical device 101. For instance, less energy may be required to create the attachment of the exposed portion 216 to the electrical contact of the component. Using less heat for the attachment may decrease the likelihood of detaching the electrical contact from an underlying attachment point. Furthermore, relatively small bond pads or other forms of electrical contacts may be used thus creating an additional savings of material.

As can be seen in FIGS. 2 and 3, the flexible circuit bodies 206 and 208 may be staked to the electrical component being connected via the exposed circuit traces. As shown in FIG. 4, the stakes 209 are positioned in relation to the contact pads 212 and 210 to receive the flexible circuit bodies 206 and 208 during assembly. As shown in FIG. 5, the flexible circuit bodies 206 and 208 may include apertures 211 nearby windows 214 that allow the stakes 209 to pass through and to allow the polyimide to be melted in the region of the apertures to bond the polyimide to the stakes 209 and thereby provide strength to the junction of the flexible circuit bodies 206 and 208 to the electrical component being connected. This may relieve some of the strain applied to the circuit trace interconnects during any movement of items within the device 101. Furthermore, as shown in FIGS. 2 and 3, the flexible circuit bodies 206 and 208 may be provided with more length than is necessary to further provide strain relief.

FIG. 6 shows another example of the primary circuit board 202' of the medical device 101 and an embodiment of the flexible circuit body 206'. In this example, the primary circuit board 202' may not be flexible or may at least be semi-rigid. Furthermore, the flexible circuit body 206' is a separate body rather than being an extension of the primary circuit board 202'. In this case, the flexible circuit body 206' may employ exposed portions of circuit traces on both the electrical component side and on the circuit board side. As shown, both sides of the flexible circuit body 206' include windows 214 and exposed portions 216.

In such a case, the primary circuit board 202' includes electrical contacts 218. These electrical contacts 218 receive attachment of the exposed portions 216 on the circuit board side of the flexible circuit body 206'. The form of attachment may be of any of the varieties also applicable to the attachment of the exposed portions 216 on the component side of the flexible circuit body 206'.

FIG. 7 illustrates an embodiment of one end of a flexible circuit body 302 where a single window 304 is formed in the insulative material 308 covering the circuit traces. The embodiments of FIGS. 5 and 6 show a single window for each exposed portion 216 of the circuit traces. In FIG. 7, the multiple circuit traces have exposed portions that extend beyond the insulative material and span the single window 304. While the window is shown in a rectangular shape, it will be appreciated that other window shapes are also applicable.

Furthermore, other embodiments may provide for exposure of the circuit trace portions 306 by omitting the insulative material forming the window. In that case, the exposed portions 306 extend freely from an end of the insulative material.

Returning to FIGS. 1-5 Stimulation therapy may be provided by embodiments of the medical device 101 having the pulse generator circuit 104 and having a feedthrough 106 located separately from the pulse generator circuit 104. Stimulation pulses are generated by the pulse generator circuit 104 and are conducted from the pulse generator circuit 104 to a circuit trace of the flexible circuit body 206. Signals are passed from the circuit trace of the flexible circuit body 206 to an electrical contact 210 of the feedthrough 106. The circuit trace includes the portion 216 exposed from the insulative body of the flexible circuit body 206 such that the portion 216 of the circuit trace is attached to the electrical contact 210 of the feedthrough 106. The signals are carried from the lead conductor 110 that is electrically coupled to the feedthrough 106 to the distal electrode 112 where stimulation is delivered to the tissue.

While embodiments have been particularly shown and described, it will be understood by those skilled in the art that various other changes in the form and details may be made therein without departing from the spirit and scope of the invention.

What is claimed is:

1. A method of constructing a medical device, comprising:
providing a flexible circuit body having at least one conductive circuit trace with an insulative body having a first external surface and a second external surface on an opposite side from the first external surface and with the first and second external surfaces covering the at least one conductive circuit trace, the at least one conductive circuit trace having a longitudinal axis and having a portion that extends along the longitudinal axis and that is exposed from the insulative body by spanning a window present in the first external surface and the second external surface of the insulative body and continuing into the insulative body between the first external surface and the second external surface on an opposite side of the window, the at least one conductive circuit trace being electrically coupled to a first circuit that produces stimulation signals, the circuit trace having a width measured within the plane of the window and perpendicular to the longitudinal axis and having a thickness measured perpendicular to the plane of the window with the width being greater than the thickness; and
attaching the portion of the circuit trace that is exposed from the insulative body to an electrical contact associated with an electrical component by using a resistive weld to create an electrical connection between the portion of the circuit trace and the electrical contact.

2. The method of claim 1, wherein the flexible circuit body has a plurality of conductive circuit traces that are covered by the insulative body and with each conductive circuit trace of the plurality having a portion that is exposed from the insulative body, the method further comprising:
attaching the portion of each of the circuit traces of the plurality to corresponding electrical contacts associated with the electrical component to create electrical connections between the portions of the circuit traces of the plurality and the corresponding electrical contacts.

3. The method of claim 2, wherein providing the flexible circuit comprises providing the flexible circuit body with the portions of each of the circuit traces spanning the window.

4. The method of claim 2, wherein providing the flexible circuit body comprises providing the flexible circuit body with a plurality of windows in the insulative body and with each of the portions of the plurality of circuit traces spanning a corresponding window of the plurality.

5. The method of claim 1, wherein providing the flexible circuit body comprises providing the portion with a conductive plating and wherein attaching comprises attaching the plated portion to the electrical contact.

6. The method of claim 1, wherein providing the flexible circuit body further comprises providing the at least one conductive circuit trace with a second portion that is exposed from the insulative body, and wherein the at least one conductive circuit trace is electrically coupled to the first circuit by attaching the second portion to an electrical contact of the first circuit.

7. The method of claim 1, wherein attaching the portion of the circuit trace comprises performing a resistance spot weld.

8. A medical device, comprising:
a housing;
a first circuit within the housing that generates stimulation pulses;
an electrical component within the housing and spaced from the first circuit, the electrical component having an electrical contact; and
a flexible circuit body within the housing and having at least one conductive circuit trace with an insulative body having a first external surface and a second external surface on an opposite side from the first external surface and with the first and second external surfaces covering the at least one conductive circuit trace, the at least one conductive circuit trace having a longitudinal axis and having a portion that extends along the longitudinal axis and that is exposed from the insulative body by spanning a window present in the first external surface and the second external surface of the insulative body and continuing into the insulative body between the first external surface and the second external surface on an opposite side of the window and that is attached to the electrical contact of the electrical component by a resistive weld to create an electrical connection between the portion of the circuit trace and the electrical contact of the electrical component, and the circuit trace being electrically coupled to the first circuit, the circuit trace having a width measured within the plane of the window and perpendicular to the longitudinal axis and having a thickness measured perpendicular to the plane of the window with the width being greater than the thickness.

9. The medical device of claim 8, wherein the electrical component has a plurality of electrical contacts, wherein the flexible circuit body has a plurality of conductive circuit traces that are covered by the insulative body and with each conductive circuit trace of the plurality having a portion that is exposed from the insulative body, and wherein the portion of each of the circuit traces of the plurality is attached to a corresponding electrical contact of the plurality of the electrical component to create electrical connections between the portions of the circuit traces of the plurality and the corresponding electrical contacts of the plurality.

10. The medical device of claim 9, wherein each of the portions of the circuit traces span the window.

11. The medical device of claim 9, wherein the flexible circuit body comprises a plurality of windows in the insulative body and each of the portions of the plurality of circuit traces spans a corresponding window of the plurality.

12. The medical device of claim 8, wherein the portion includes a conductive plating and the conductive plating is attached to the electrical contact.

13. The medical device of claim 8, wherein the at least one conductive circuit trace comprises a second portion that is exposed from the insulative body, and wherein electrically coupling the at least one conductive circuit trace to the first circuit comprises attaching the second portion to an electrical contact of the first circuit.

14. The medical device of claim 8, wherein the portion of the circuit trace is attached by a resistance spot weld to the electrical contact of the electrical component.

15. A method of providing stimulation therapy from a medical device having a pulse generator circuit and having a feedthrough located separately from the pulse generator circuit, comprising:
    generating stimulation pulses by the pulse generator circuit;
    conducting the stimulation pulses from the pulse generator circuit to a circuit trace of a flexible circuit body;
    passing the signals from the circuit trace of the flexible circuit body to an electrical contact of the feedthrough, the circuit trace having a longitudinal axis and having a portion that extends along the longitudinal axis and that is exposed from an insulative body of the flexible circuit body that has a first external surface and a second external surface on an opposite side from the first external surface where the first and second external surfaces cover the circuit trace by spanning a window present in the first external surface and the second external surface of the insulative body and continuing into the insulative body between the first external surface and the second external surface on an opposite side of the window such that the portion of the circuit trace is attached to the electrical contact of the feedthrough by a resistive weld, the circuit trace having a width measured within the plane of the window and perpendicular to the longitudinal axis and having a thickness measured perpendicular to the plane of the window with the width being greater than the thickness; and
    carrying the signals from a lead conductor electrically coupled to the feedthrough to the electrode.

16. The method of claim 15, wherein the feedthrough has a plurality of electrical contacts, wherein the flexible circuit body has a plurality of conductive circuit traces that are covered by the insulative body and with each conductive circuit trace of the plurality having a portion that is exposed from the insulative body, and wherein the portion of each of the circuit traces of the plurality is attached to a corresponding electrical contact of the plurality on the feedthrough to create electrical connections between the portions of the circuit traces of the plurality and the corresponding electrical contacts of the feedthrough.

17. The method of claim 16, wherein each of the portions of the circuit traces span the window.

18. The method of claim 16, wherein the flexible circuit body comprises a plurality of windows in the insulative body and each of the portions of the plurality of circuit traces spans a corresponding window of the plurality.

19. The method of claim 15, wherein the portion includes a conductive plating and the conductive plating is attached to the electrical contact.

20. The method of claim 15, wherein the at least one conductive circuit trace comprises a second portion that is exposed from the insulative body, and wherein the at least one conductive circuit trace is electrically coupled to an electrical contact of the pulse generator circuit by an attachment of the second portion to the electrical contact of the pulse generator.

21. The method of claim 15, wherein the portion of the circuit trace is attached by a resistance spot weld to the electrical contact of the first circuit board.

22. A method of constructing a medical device, comprising:
    providing a flexible circuit body having at least one conductive circuit trace with an insulative body having a first external surface and a second external surface on an opposite side from the first external surface and with the first and second external surfaces covering the at least one conductive circuit trace, the at least one conductive circuit trace having a longitudinal axis and having a portion that extends along the longitudinal axis and that is exposed from the insulative body by spanning a window present in the first external surface and the second external surface of the insulative body and continuing into the insulative body between the first external surface and the second external surface on an opposite side of the window, the at least one conductive circuit trace being electrically coupled to a first circuit that produces stimulation signals, the exposed portion having a same width as a remainder of the circuit trace within the insulative body, the width of the circuit trace being measured within the plane of the window and perpendicular to the longitudinal axis and the circuit trace having a thickness measured perpendicular to the plane of the window with the width being greater than the thickness; and
    attaching the portion of the circuit trace that is exposed from the insulative body to an electrical contact associated with an electrical component to create an electrical connection between the portion of the circuit trace and the electrical contact.

23. A medical device, comprising:
    a housing;
    a first circuit within the housing that generates stimulation pulses;
    an electrical component within the housing and spaced from the first circuit, the electrical component having an electrical contact; and
    a flexible circuit body within the housing and having at least one conductive circuit trace with an insulative body having a first external surface and a second external surface on an opposite side from the first external surface and with the first and second external surfaces covering the at least one conductive circuit trace, the at least one conductive circuit trace having a longitudinal axis and having a portion that extends along the longitudinal axis and that is exposed from the insulative body by spanning a window present in the first external surface and the second external surface of the insulative body and continuing into the insulative body between the first external surface and the second external surface on an opposite side of the window and that is attached to the electrical contact of the electrical component to create an electrical connection between the portion of the circuit trace and the electrical contact of the electrical component, the exposed portion having a same width as a remainder of the circuit trace within the insulative body, and the circuit trace being electrically coupled to the first circuit, the width of the circuit trace being measured within the plane of the window and perpendicular to the longitudinal axis and the circuit trace having a thickness measured perpendicular to the plane of the window with the width being greater than the thickness.

24. A method of providing stimulation therapy from a medical device having a pulse generator circuit and having a feedthrough located separately from the pulse generator circuit, comprising:
    generating stimulation pulses by the pulse generator circuit;

conducting the stimulation pulses from the pulse generator circuit to a circuit trace of a flexible circuit body;

passing the signals from the circuit trace of the flexible circuit body to an electrical contact of the feedthrough, the circuit trace having a longitudinal axis and having a portion that extends along the longitudinal axis and is exposed from an insulative body of the flexible circuit body that has a first external surface and a second external surface on an opposite side from the first external surface where the first and the second external surfaces cover the circuit trace by spanning a window present in the first external surface and the second external surface of the insulative body and continuing into the insulative body between the first external surface and the second external surface on an opposite side of the window such that the portion of the circuit trace is attached to the electrical contact of the feedthrough, the exposed portion having a same width as a remainder of the circuit trace within the insulative body, the width of the circuit trace being measured within the plane of the window and perpendicular to the longitudinal axis and the circuit trace having a thickness measured perpendicular to the plane of the window with the width being greater than the thickness; and carrying the signals from a lead conductor electrically coupled to the feedthrough to the electrode.

* * * * *